United States Patent
Pardoel et al.

(10) Patent No.: US 9,616,206 B2
(45) Date of Patent: Apr. 11, 2017

(54) ELECTRONIC PILL FOR DELIVERY OF POWDER MEDICATION

(75) Inventors: Michel Gerardus Pardoel, Mierlo (NL); Hans Zou, Chappaqua, NY (US); Jeff Shimizu, Cortlandt Manor, NY (US)

(73) Assignee: Medimetrics Personalized Drug Delivery, Charlotte, NC (US)

( * ) Notice: Subject to any disclaimer, the term of this patent is extended or adjusted under 35 U.S.C. 154(b) by 124 days.

(21) Appl. No.: 13/879,003

(22) PCT Filed: Sep. 29, 2011

(86) PCT No.: PCT/IB2011/054280
§ 371 (c)(1),
(2), (4) Date: Oct. 6, 2014

(87) PCT Pub. No.: WO2012/046166
PCT Pub. Date: Apr. 12, 2012

(65) Prior Publication Data
US 2015/0141967 A1 May 21, 2015

(30) Foreign Application Priority Data
Oct. 6, 2010 (EP) .................................... 10186712

(51) Int. Cl.
*A61M 31/00* (2006.01)
(52) U.S. Cl.
CPC ..... *A61M 31/002* (2013.01); *A61M 2202/064* (2013.01)
(58) Field of Classification Search
CPC .......... A61M 31/002; A61M 2202/064; A61M 31/00; A61M 2205/3523; A61M 15/0028;
(Continued)

(56) References Cited

U.S. PATENT DOCUMENTS 3,118,439 A * 1/1964 Perrenoud .............. A61B 5/073
169/26
4,416,659 A * 11/1983 Simpson et al. ................ 604/48
(Continued)

FOREIGN PATENT DOCUMENTS

| CN | 1600279 | 3/2005 |
| CN | 101516257 | 8/2009 |
| WO | WO2009104110 | 8/2009 |

OTHER PUBLICATIONS

Translated Chinese Office Action mailed Nov. 21, 2014 for Chinese patent application No. 201180058764.0, a counterpart foreign application of U.S. Appl. No. 13/879,003, 18 pages.

*Primary Examiner* — Scott Medway
(74) *Attorney, Agent, or Firm* — Lee & Hayes, PLLC (57) ABSTRACT

The invention relates to an electronic pill (102) for delivery of a medication (104) inside a mammal. The electronic pill (102) comprises a reservoir (106) for releasing the medication (104) in response to a predefined level of pressure. Furthermore a primary elastic element (108) is comprised for applying said predefined level of pressure to the reservoir (106) via a piston (110) upon release from the piston (110) of its constrained position. The piston (110) in its turn, when in constrained position, induces a predefined level of stress in the primary elastic element (108) by accordingly deforming it. The electronic pill (102) comprises a mechanism (114) for changing, upon actuation, from a constraining configuration in which the piston (110) is maintained at its constrained position to a releasing configuration in which the piston (110) is released. The mechanism (112) limits the displacement of the piston (110) during changing between said configurations to a level which is substantially smaller than the deformation introduced in the primary elastic element (108).

20 Claims, 6 Drawing Sheets

(58) Field of Classification Search
CPC ..... A61B 10/0045; A61B 1/041; A61B 5/073;
A61B 1/00016; A61B 5/4839; A61J 3/07
See application file for complete search history.

(56) References Cited

U.S. PATENT DOCUMENTS

| | | | |
|---|---|---|---|
| 5,217,449 A | 6/1993 | Yuda et al. | |
| 5,395,366 A * | 3/1995 | D'Andrea | A61B 5/0031 604/114 |
| 6,186,141 B1 * | 2/2001 | Pike et al. | 128/203.12 |
| 7,772,796 B2 * | 8/2010 | Farritor | A61B 1/00158 104/138.1 |
| 8,702,597 B2 * | 4/2014 | Iddan | A61B 1/00094 600/167 |
| 2004/0253304 A1 * | 12/2004 | Gross | A61B 1/041 424/451 |
| 2010/0189779 A1 * | 7/2010 | Herbert et al. | 424/451 |

\* cited by examiner

ELECTRONIC PILL FOR DELIVERY OF POWDER MEDICATION

PRIORITY APPLICATION

This Application is a 35 U.S.C. 371 National Stage Entry of and claims priority to PCT Application Serial No. PCT/IB2011/054280, entitled "Electronic Pill for Delivery of Powder Medication," filed on Sep. 29, 2011, and European Patent Application No. 10186712.5, entitled "Electronic Pill for Delivery of Powder Medication," filed on Oct. 6, 2010, both of which are fully incorporated by reference herein.

FIELD OF THE INVENTION

The invention relates to an electronic pill for delivery of a medication inside a mammal.

BACKGROUND OF THE INVENTION

CN 1600279 discloses a localizable medicine releasing device comprising an electronic capsule which consists of a shell, a battery, a remotely controlled module having a miniature heating element, a pre-stressed spring, a piston fixed by a polymer thread, a medicine chamber and a medicine releasing channel. The miniature heating element fuses off the polymer thread when the remotely controlled module receives a control signal. As a result, the piston is allowed to move, under the action of the pre-stressed spring, as to open the medicine releasing channel for releasing the medicine.

The device disclosed in CN 1600279 employs a polymer thread to constrain the piston. Movement of the piston is initiated by fusing the polymer thread via the heating element. Such fusing has the character of a continuous rather than a discrete process. As a result the force with which the polymer thread fixes the piston against movement gradually reduces. Namely, by heating the polymer, which must be a thermoplastic i.e. a thermosoftening plastic rather than a thermosetting plastic, the modulus of elasticity is reduced and consequently the amount of strain in the polymer is increased. Owing to said strain increase the piston is allowed to significantly displace before the polymer thread breaks in two. Therefore the speed with which the piston impacts the medicine is negligible thereby dissipating the contribution of the piston's impulse in releasing the medication from the device. As to compensate such absence of impulse, the spring is required to have a relatively large mechanical stiffness. Said requirement on mechanical stiffness imposes lower bounds 25 on e.g. the spring's coil diameter or compression length thereby increasing the dimensions of the device which is to accommodate said spring. As a result, a problem of the device disclosed in CN 1600279 is in its relatively large dimensions.

SUMMARY OF THE INVENTION

It is an object of the invention to provide a system of the kind defined in the opening paragraph having smaller dimensions.

The object of the invention is achieved by the electronic pill according to the invention for delivery of a medication inside a mammal. The electronic pill according to the invention comprises a reservoir configured for releasing the medication in response to a predefined level of pressure, a primary elastic element for applying said predefined level of pressure to the reservoir via a piston upon release from the piston of its constrained position, which piston, when in constrained position, is arranged for inducing a predefined level of stress in the primary elastic element by introducing an accompanying corresponding level of deformation therein, and a mechanism configured for changing, upon actuation, from a constraining configuration which is arranged for maintaining the piston in its constrained position to a releasing configuration which is arranged for releasing the piston from its constrained position, wherein the mechanism limits the displacement of the piston during changing from said constraining configuration to said releasing configuration to a level substantially smaller than the deformation introduced in the primary elastic element.

By limiting the piston's displacement during changing from the constraining configuration to the releasing configuration, the level of deformation introduced by the piston in the primary elastic element is accordingly maintained. As a result, a significant share of the predefined level of stress in the primary elastic element is preserved while changing from the constraining configuration to the releasing configuration. This share is discretely released when the mechanism attains the releasing configuration which enables the primary elastic element to accelerate the piston and the reservoir relative to one another such that they can mutually impact at relatively high velocity. Depending on the mass of the piston relative to that of the electronic pill including the reservoir and the medication, the relative acceleration of the piston and the reservoir will encompass an acceleration of the piston, an acceleration of the electronic pill or a combination thereof. Obviously, said contributions to the relative acceleration only come apparent when using a coordinate system that is neither fixed in space. The impulses of the piston and/or the electronic pill significantly contribute to applying the predefined level of pressure to the reservoir. Consequently, as to release the medication from the reservoir, the predefined level of stress induced in the primary elastic element may be smaller. As a result the primary elastic element is allowed to have a smaller mechanical stiffness or to be provided with a smaller level of deformation. Both options enable the electronic pill to have smaller dimensions.

Owing to aforementioned miniaturization, the electronic pill according to the invention allows for easier swallowing by the mammal thereby increasing patient compliance.

The primary elastic element may be any element having an elastic characteristic i.e. reversibly deforming upon application of stress, said elastic characteristic including but not limited to Hooke's law of linear elasticity. Therefore the elastic element may be a compression spring, a torsion spring, a leaf spring but equally well a cylinder filled with a compressible gas.

In this text substantially smaller means at least 5 times smaller. Hence, by limiting the piston's displacement during changing from constraining to releasing configuration to a level substantially smaller than the deformation introduced in the primary elastic element, at least 80% of the deformation introduced into the primary elastic element is preserved. As a result, if the primary elastic element obeys Hooke's law of linear elasticity, 80% of the predefined level of stress is maintained after changing from constraining configuration to releasing configuration.

In a preferred embodiment of the electronic pill according to the invention the primary elastic element is a helical spring. A helical spring comprises windings that are wounded around an imaginary cylinder. Owing to this imaginary cylinder, contrary to e.g. a cartridge filled with a fluid, the helical spring occupies a relatively small volume.

Therefore this embodiment has the advantage of further reducing the dimensions of the electronic pill.

A further preferred embodiment of the electronic pill according to the invention comprises an actuator for actuating the mechanism upon receiving of an external trigger. Herein, an external trigger is distinguished from an internal trigger in that it is either directly or indirectly dependent on external changes. This embodiment advantageously enables adapting the release of medication to changes in circumstances external of the electronic pill.

A further preferred embodiment of the electronic pill according to the invention comprises a primary module and a secondary module, wherein the primary module is configured for accommodating at least the primary elastic element, the mechanism and the reservoir, wherein the secondary module is arranged for accommodating at least the actuator, and wherein the primary module and the secondary module are mutually releasably connectable. This embodiment allows the medication reservoir to be handled separately from the secondary module before and after releasing medication. Therefore this embodiment effectively facilitates easy quality control for medication-filling procedure that has to be compliant to stringent regulations. As a result, this embodiment also advantageously increases the economic feasibility of reusing the secondary module.

A further preferred embodiment of the electronic pill according to the invention comprises a sensor for measuring a body parameter and for generating the external trigger in response thereto. This embodiment advantageously enables targeting the release of medication to the body parameter under consideration thereby increasing medical efficacy.

In a further preferred embodiment of the electronic pill according to the invention, the mechanism comprises a secondary elastic element configured for changing from the constraining configuration to the releasing configuration. After releasing the piston from its constrained position, the secondary elastic element causes the mechanism, due to its elastic properties, to return to the constraining configuration. This embodiment is in advantageous in that it reduces the power required to release medication from the reservoir. The force and consequently power required to cause the secondary element to change from the constraining configuration to the releasing configuration, is substantially smaller than the force thus power stored in the primary elastic element and which is exerted in the releasing configuration. As a result, this embodiment circumvents the need for a power source capable of sustaining extremely high current drains. A further advantage of this embodiment is in its capability to increase power efficiency. Once swallowed, the electronic pill is subject to high levels of moisture that negatively heating efficiency. The electronic pill according to the invention effectively circumvents such limited heating efficiency by employing elasticity rather than heating to enable changing from the constraining to the releasing configuration. This embodiment furthermore has the advantage that it facilitates reusing a module comprising the mechanism in combination with a fresh reservoir as the requirement that the mechanism is to be in the constraining configuration upon mutually connecting the module and the reservoir is automatically fulfilled.

In a further preferred embodiment of the electronic pill according to the invention, the secondary elastic element is a leaf spring. This embodiment is advantageous in that it enables further miniaturization of the electronic pill owing to the relatively slender geometry that marks a leaf spring.

A further preferred embodiment of the electronic pill according to the invention comprises an inclined plane moveable relative to the leaf spring and connected slideable thereto and configured for inducing a predefined level of stress in the leaf spring in the constraining configuration, and upon moving due to actuation, for releasing said predefined level of stress from the leaf spring. An inclined plane is a flat surface whose endpoints are located at different heights. By moving the inclined plane relative to the leaf spring such that the leaf spring is adjacent to the higher endpoint of the inclined plane, a predefined level of stress is induced in the leaf spring as it is forced to deform because of the inclination of the inclined plane. Compared to moving the leaf spring towards the higher end point along a vertical track, the inclined plane enables performing the same amount of work on the basis of a smaller force exerted over a larger distance. As a result, it is made feasible by this embodiment to induce the predefined level of stress in the leaf spring using an actuator provided with relatively little power and having correspondingly small dimensions. Therefore, this embodiment is advantageous in that it enables further miniaturization of the electronic pill.

In a practical embodiment of the electronic pill according to the invention, the inclined plane is connected to a movable nut which is driveable by the actuator. Preferably the actuator is provided with a rotatable screw for cooperation with the nut. Because a screw basically is an inclined plane folded around a cylinder, this embodiment enables performing the work required to displace the nut, however, on the basis of a smaller force or torque exerted over a larger distance or a larger angular displacement, respectively. This enables further miniaturization of the electronic pill.

In a further preferred embodiment of the electronic pill according to the invention, the mechanism comprises a lever for changing from the constraining configuration to the releasing configuration, wherein a first extremity is of the lever is configured for temporarily constraining the piston and wherein a second extremity of the lever is configured for being actuated. This embodiment guarantees that the piston's displacement during changing from the constraining configuration to the releasing configuration is zero. As a result a maximum share i.e. 100% of the predefined level of stress is preserved in the primary elastic element while changing configurations. Therefore the impulse of the piston is enabled to maximally contribute to applying the predefined level of pressure to the reservoir. Consequently, for the purpose of releasing the medication from the reservoir, the predefined level of stress may be smaller. This allows the primary elastic element to be provided with smaller dimensions. As a result this embodiment enables further reducing the dimensions of the electronic pill. This embodiment is furthermore advantageous in that it reduces the power required to release medication from the reservoir. The force and consequently power required to cause the lever to change from the constraining configuration to the releasing configuration, is substantially smaller than the force thus power stored in the primary elastic element and which is exerted in the releasing configuration. As a result, this embodiment circumvents the need for a power source capable of sustaining extremely high current drains. A further advantage of this embodiment is in its capability to increase power efficiency. Once swallowed, the electronic pill is subject to high levels of moisture that negatively heating efficiency. The electronic pill according to the invention effectively circumvents such limited heating efficiency by employing the lever than heating to initiate changing from the constraining to the releasing configuration.

In a further preferred embodiment of the electronic pill according to the invention, a distance between the first extremity and a pivot point associated with the lever is substantially smaller than a further distance between the second extremity and said pivot point. By making the distance between the pivot point and the first extremity point substantially small compared to the further distance between the second extremity and the pivot point, substantial leverage is created for the force to be exerted on the second extremity by the actuator. As a result this embodiment allows for changing from the constraining situation to the releasing configuration using a relatively small level of force consistent with the aforementioned leverage. As a result this embodiment effectively reduces the level of power the actuator is required to have and thereby reduces the actuator's dimensions. Therefore this embodiment has the advantage of enabling further miniaturization of the electronic pill.

In a further practical embodiment of the electronic pill according to the invention, the second extremity is connected to a movable nut which is driveable by the actuator. Preferably the actuator is provided with a rotatable screw for cooperation with the nut. As explained before, a screw is an inclined plane folded around a cylinder and therefore this embodiment enables performing the work required to displace the nut employing a smaller force or torque exerted over a larger distance or a larger angular displacement, respectively. This enables reducing the actuator's power and consequently the actuator's outer dimensions thereby providing for further miniaturization of the electronic pill.

DETAILED DESCRIPTION OF THE EMBODIMENTS

Figure 1A:
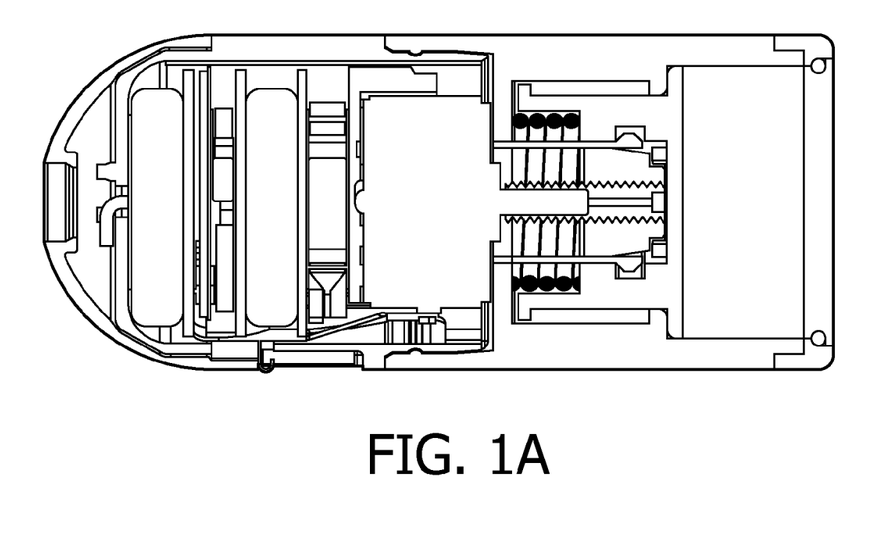
FIG. 1A schematically displays a first embodiment of the electronic pill according to the invention comprising a secondary elastic element, wherein the mechanism is in the constraining configuration.

FIGS. 1A, 1B, 1C and 1D schematically display an electronic pill 102 for delivery of a medication 104 in a mammal (not shown). The electronic pill 102 comprises a reservoir 106 for storing the medication 104 and for releasing it in response to a predefined level of pressure applied thereto. The electronic pill 102 furthermore comprises a primary elastic element 108 for applying said predefined level of pressure to the reservoir 106 via a piston 110 upon release of piston 110 of its constrained position. FIG. 1A displays the piston 110 situated in said constrained position. In this specific example the primary elastic element 108 is a helical spring 112. Referring to FIG. 1A, the piston 110 is arranged for inducing a predefined level of stress in the primary elastic element 108 by introducing an accompanying corresponding level of deformation therein. Electronic pill 102 furthermore comprises a mechanism 114 configured for changing, upon actuation, from a constraining configuration as displayed in FIG. 1A and arranged for maintaining the piston 110 in its constrained position, to a releasing configuration as displayed in FIG. 1B and arranged for releasing the piston 110 from its constrained position. The mechanism 114 limits the displacement of the piston 110 during changing from said constraining configuration to said releasing configuration to a level substantially smaller than the deformation introduced in the primary elastic element 108. The deformation introduced in the primary elastic element 108 comes apparent from comparing FIG. 1A with FIG. 1C which depicts the piston released from its constrained position thereby allowing the primary elastic element 108 to attain its undeformed configuration. Apparently, in this specific embodiment the deformation induced by the piston 110 into the primary elastic element 108 amounts to roughly 50% as the undeformed length is roughly twice the deformed length, see FIGS. 1B and 1A, respectively.

The mechanism 114 optionally comprises a secondary elastic element 116 for changing from the constraining configuration to the releasing configuration. The secondary elastic element 116 is embodied by a leaf spring 118 in this specific case.

In this specific embodiment electronic pill 102 comprises an actuator 120 for actuating the mechanism 114 and more specifically the leaf spring 118 upon receiving of an external trigger. Such external trigger may be generated by a sensor 121 which is configured for measuring a parameter inside the mammal and for generating said external trigger in response thereto. A particular parameter of interest is pH as it is indicative for the electronic pill's position inside the gastrointestinental tract. An energy source 123 for providing the actuator 120 and the sensor 121 with power is optionally comprised in the electronic pill 102.

Figure 1B:
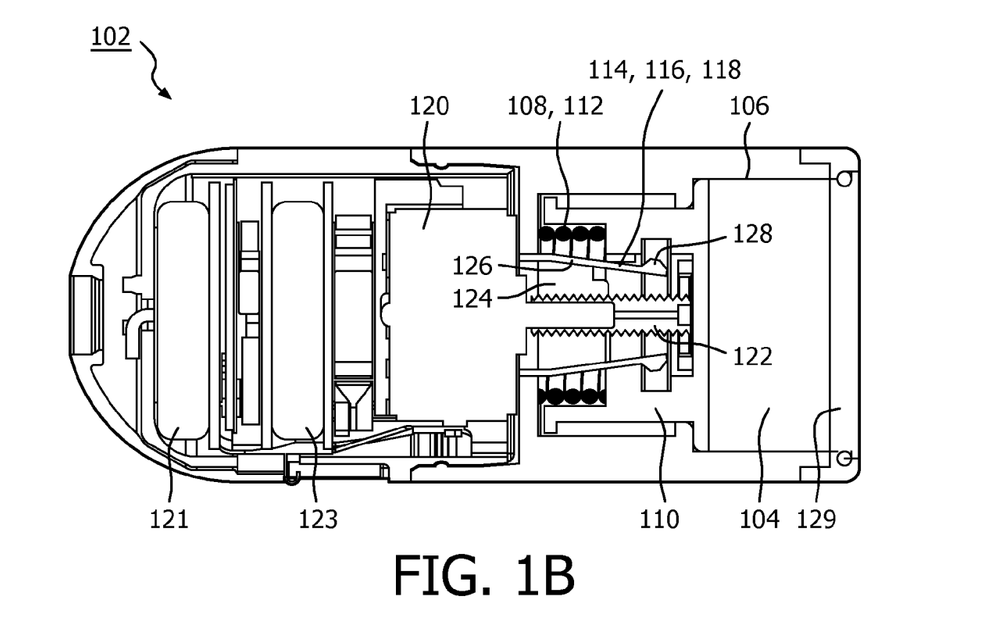
FIG. 1B schematically depicts the first embodiment of the electronic pill according to the invention, wherein the mechanism occupies the releasing configuration.
Figure 1C:
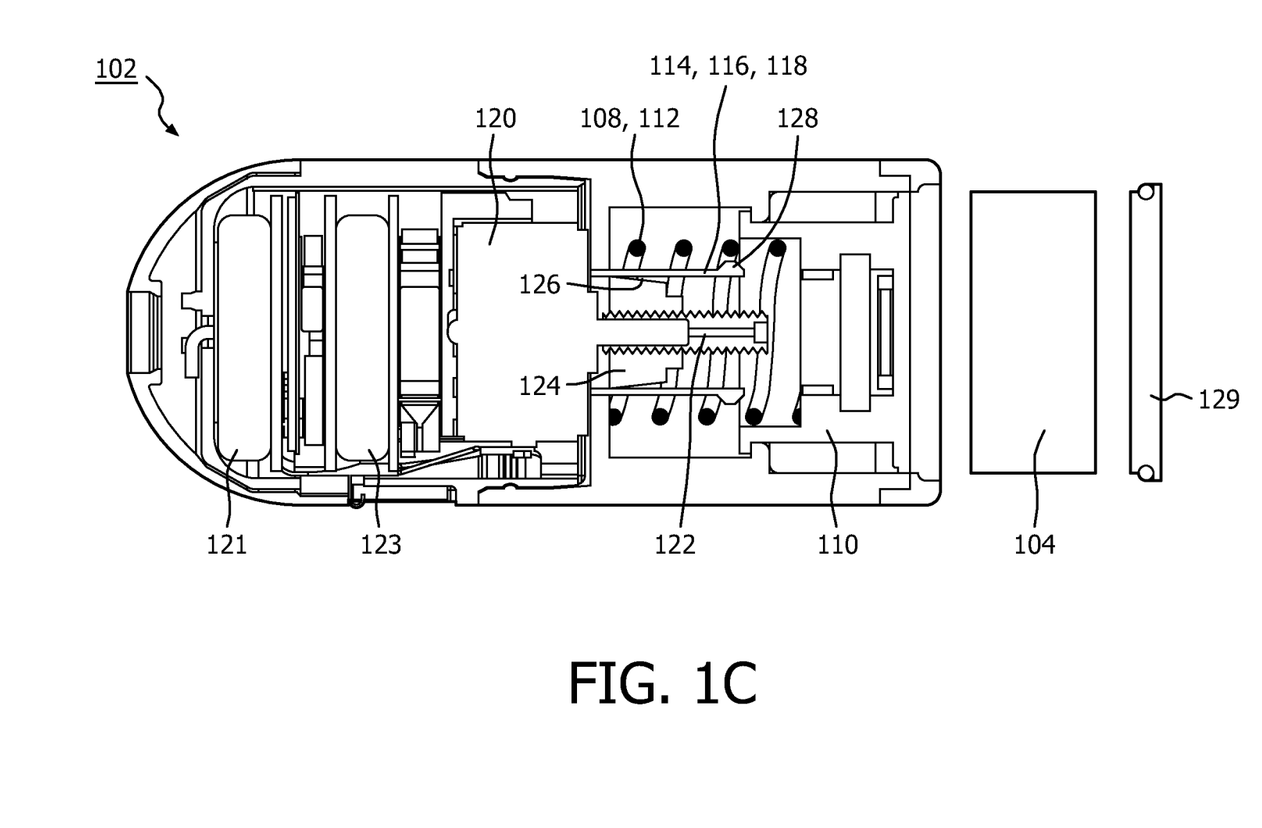
FIG. 1C schematically shows the first embodiment of the electronic pill according to the invention at an instance after the medication has been released from the reservoir.

The actuator 120 may be provided with a rotatable screw 122, e.g. a stepper motor whose axis is equipped with an external threading, for cooperation with a moveable nut 124 provided with an inclined plane 126 thereby performing as a wedge. Obviously, the moveable nut 124 may be provided with more than a single inclined plane e.g. for reasons of symmetry. The inclined plane 126, i.e. a plane having some angle of inclination, is movable relatively to the leaf spring 118 and connected slideable thereto. The inclined plane 126 is configured for inducing a predefined level of stress in the leaf spring 118 when the mechanism 114 is in the constraining configuration see FIG. 1A, and upon moving due to actuation by the actuator 120, for releasing said predefined level of stress from the leaf spring see FIG. 1B. That is, the transition from the constraining configuration to the releasing configuration upon actuation is accompanied by the nut 124 moving in a direction such that the inclination of the inclined plane 126 allows the leaf spring 118 to bend inwards i.e. away from the piston 110. Referring to FIG. 1B, the leaf spring 118 gives way to the piston 110 once the plug 128 mounted at the leaf spring no longer obstructs the piston 110 from moving towards the medication 104. In this particular embodiment the mass of the piston 110 is substantially smaller than the mass associated with the reaming features of electronic pill 102. Therefore, the piston 110 is accelerated towards the medication in response to the predefined level of stress stored in the primary elastic element 108. As a result the piston 110 causes the pressure in the medication 104 to exceed the predefined level. In response thereto, referring to FIG. 1C, the lid 129 breaks off and the reservoir 106 releases the medication 104. In order to have the lid 129 appropriately i.e. predictably and as a whole break away in response to the predefined level of pressure, the lid 129 must be substantially mechanically stiff relative to its connection to the reservoir 106. After giving way to the piston 110, the leaf 118 is allowed to attain its undeformed configuration, see FIG. 1C.

Comparing FIGS. 1A and 1B, the displacement of the piston 110 during the transition of the mechanism 112 from its constraining to its releasing configuration is considerably less than the amount of deformation introduced by the piston 110 to the primary elastic element 108. More specifically, by decreasing the length of the plug 128 projected on the leaf spring 118, the piston's displacement may be further reduced.

Figure 1D:
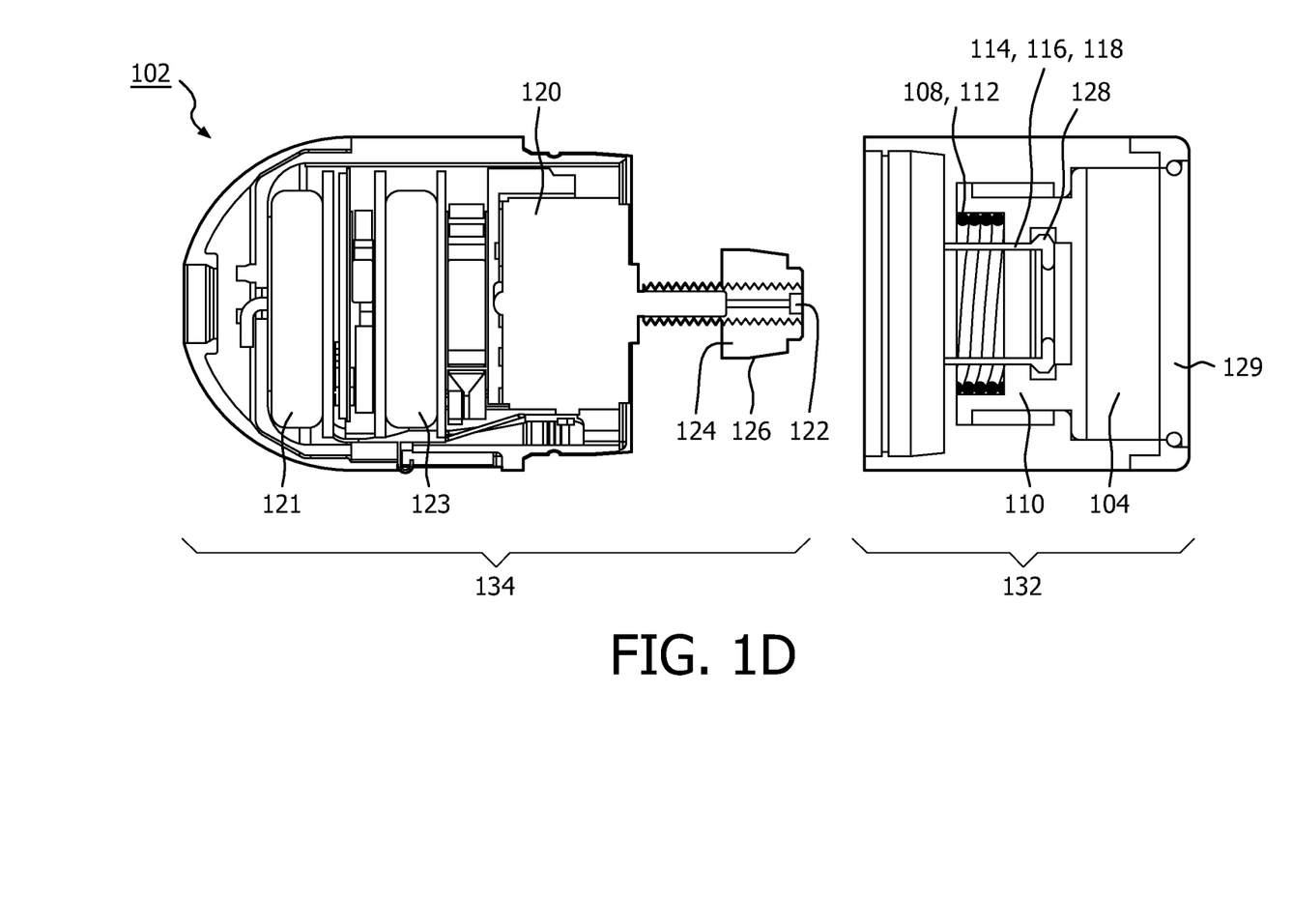
FIG. 1D schematically depicts the first embodiment of the electronic pill according to the invention furthermore comprising a primary module and a secondary module.

Referring FIG. 1D, the electronic pill 102 may comprise a primary module 132 and a secondary module 134. The primary module 132 is configured for accommodating at least the primary elastic element 108, the mechanism 114 and the reservoir 106, but may equally well accommodate the secondary elastic element 116. The secondary module 134 is arranged for accommodating at least the actuator 120, but preferably also accommodates the sensor 121, the energy source 123 and the movable nut 124. Primary module 132 and secondary module 134 are mutually releasably connectable which allows for reuse of the secondary module 134.

Figure 2A:
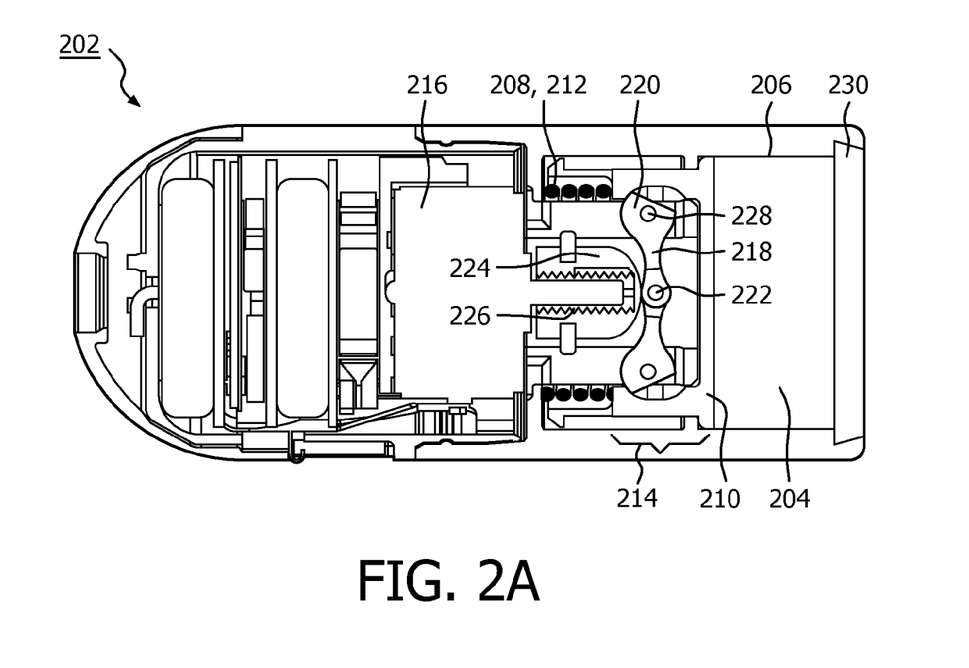
FIG. 2A schematically depicts a second embodiment of the electronic pill according to the invention comprising a lever for changing from the constraining to the releasing configuration, wherein the mechanism is in the constraining configuration.
Figure 2B:
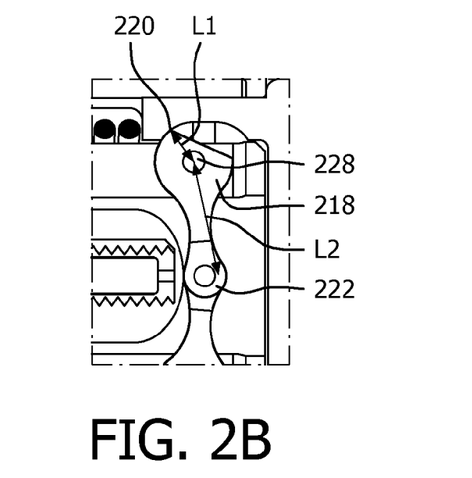
FIG. 2B provides an enlarged view for part of FIG. 2A.

FIGS. 2A, 2B, 2C and 2D schematically display an electronic pill 202 for delivery of a medication 204 in a mammal (not shown). The electronic pill 202 comprises a reservoir 206 for storing the medication 204 and for releasing it in response to a predefined level of pressure applied thereto. The electronic pill 202 furthermore comprises a primary elastic element 208 for applying said predefined level of pressure to the reservoir 206 via a piston 210 upon release of piston 210 of its constrained position. FIG. 2A displays the piston 110 situated in said constrained position. In this specific example the primary elastic element 208 is a helical spring 212. Referring to FIG. 2A, the piston 210 is arranged for inducing a predefined level of stress in the primary elastic element 208 by introducing an accompanying corresponding level of deformation therein. Electronic pill 202 furthermore comprises a mechanism 214 configured for changing, upon actuation, from a constraining configuration as displayed in FIG. 2A and arranged for maintaining the piston 210 in its constrained position, to a releasing configuration as displayed in FIG. 2C and arranged for releasing the piston 210 from its constrained position. The mechanism 214 limits the displacement of the piston 210 during changing from said constraining configuration to said releasing configuration to a level substantially smaller than the deformation introduced in the primary elastic element 208.

In this particular embodiment electronic pill 202 comprises an actuator 216 for actuating the mechanism 214 upon receiving of an external trigger. The mechanism 214 optionally comprises a lever 218 for changing from the constraining configuration to the releasing configuration. A first extremity 220 of the lever 218 is configured for temporarily constraining the piston 210 whereas a second extremity 222 of the lever 218 is configured for being actuated. For that purpose, the second extremity 222 is connected to a movable nut 224 which is driveable by the actuator 216. In order to drive the nut 224, the actuator 216 is for instance provided with a rotatable screw 226 for cooperation with the nut 224 that is equipped with a matching internal threading (not shown) for this purpose. Preferably, in order to create mechanical leverage, a distance L2 between the second extremity 222 and a pivot point 228 of the lever 218 is substantially larger than a distance L1 between the first extremity 220 and said pivot point, see FIG. 2B.

Figure 2C:
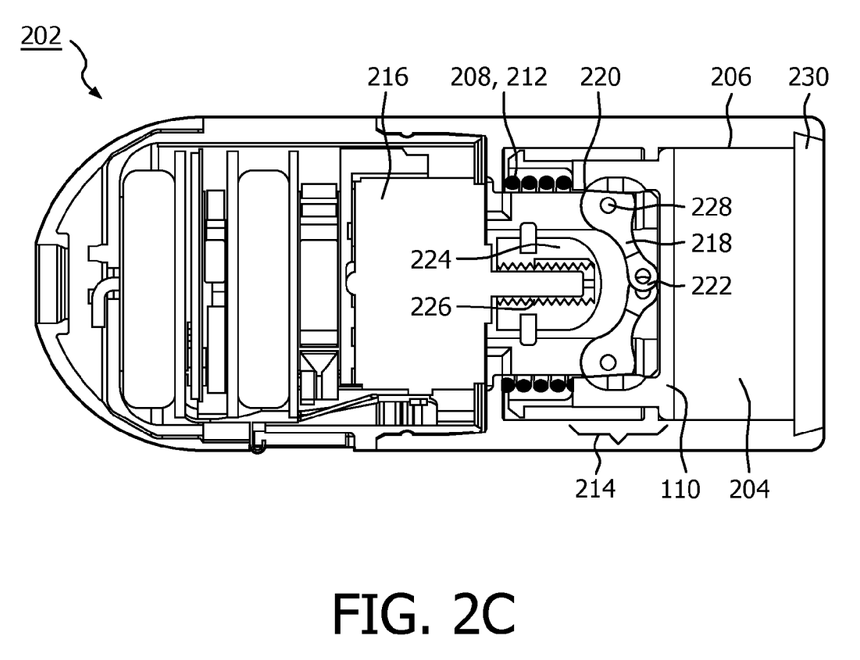
FIG. 2C schematically depicts the second embodiment of the electronic pill according to the invention, wherein the mechanism occupies the releasing configuration.
Figure 2D:
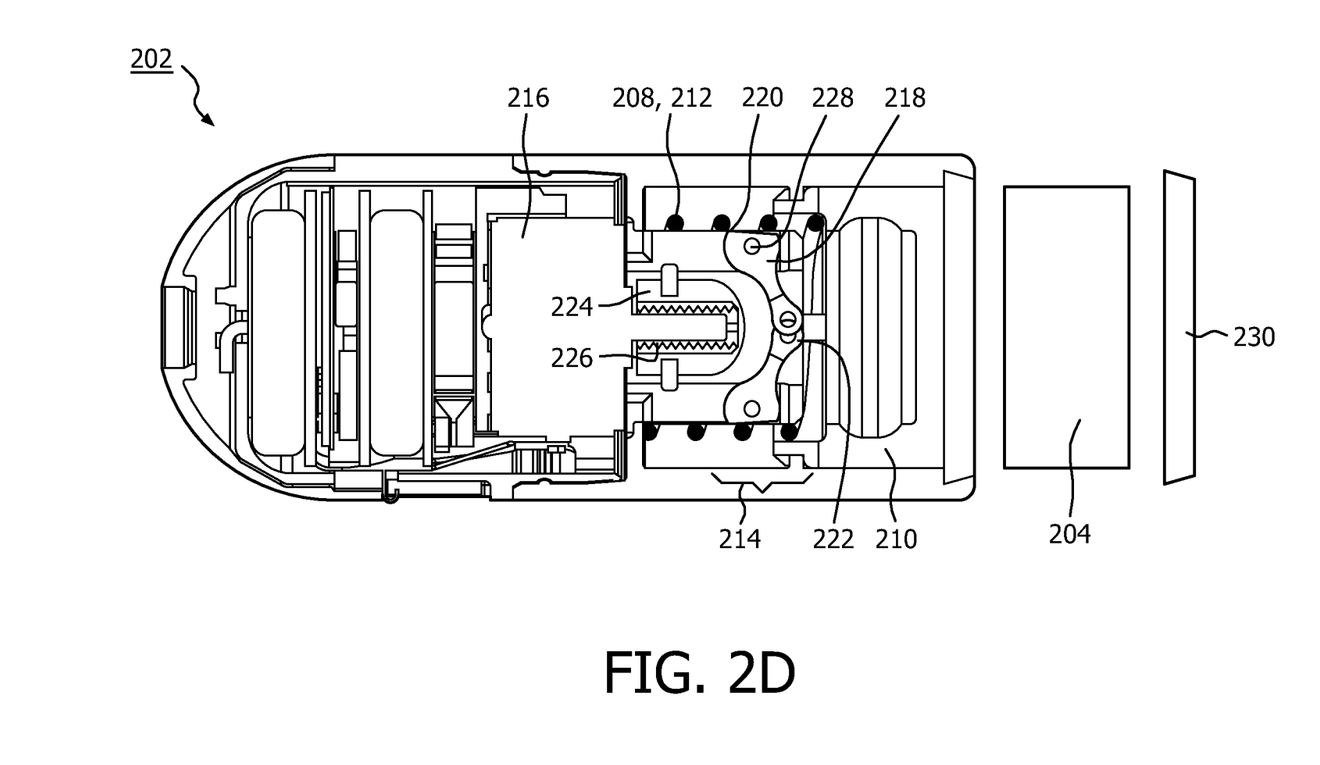
FIG. 2D schematically shows the second embodiment of the electronic pill according to the invention at an instance after the medication has been released from the reservoir.

Comparing FIGS. 2A and 2C, the transition from the constraining configuration to the releasing configuration is accompanied by the nut 224 and hence the second extremity 222 moving in a direction which causes the first extremity 220 to no longer obstruct the piston 210 from moving towards the medication 204. Thereafter the piston 210 is accelerated towards the medication in response to the predefined level of stress stored in the primary elastic element 208. As a result the piston 210 causes the pressure in the medication 204 to exceed the predefined level. In response thereto, referring to FIG. 2D, the reservoir 206 releases the medication 204 after breaking away of lid 230 in response to the predefined level of pressure. The displacement of the piston 210 during the transition of the mechanism 212 from its constraining to its releasing configuration is zero.

Electronic pill 202 perfectly allows for a separation into a primary and a secondary module similar to electronic pill 102, thereby facilitating reuse of at least a part of electronic pill 202.

While the invention has been illustrated and described in detail in the drawings and in the foregoing description, the illustrations and the description are to be considered illustrative or exemplary and not restrictive. The invention is not limited to the disclosed embodiments. It is noted that the system according to the invention and all its components can be made by applying processes and materials known per se. In the set of claims and the description the word "comprising" does not exclude other elements and the indefinite article "a" or "an" does not exclude a plurality. Any reference signs in the claims should not be construed as limiting the scope. It is further noted that all possible combinations of features as defined in the set of claims are part of the invention.

The invention claimed is:

1. An electronic pill for delivery of a medication inside a mammal, comprising:
   a reservoir configured for releasing the medication in response to application of a predefined level of pressure on the reservoir;
   a piston configured to act on the reservoir and movable between a constrained position and a release position spaced from the constrained position;
   a primary elastic element for applying said predefined level of pressure to the reservoir via the piston upon release of the piston from its constrained position, wherein the piston, in the constrained position, deforms the primary elastic element to induce a predefined level of stress in the primary elastic element; and
   a mechanism movable relative to the piston and the primary elastic element between a constraining configuration arranged to maintain the piston in its constrained position and a releasing configuration in which the piston is free to move to the release position;
   an actuator having a threaded shaft; and
   a threaded nut engaging the threaded shaft and acting on the mechanism, the threaded nut being movable, by the actuator, along a longitudinal axis of the pill between a first position and a second position, the second position being spaced from the first position, wherein, in the first position, the threaded nut retains the mechanism in the constraining configuration and, in the second position, the threaded nut causes the mechanism to move to the releasing configuration.

2. The electronic pill according to claim 1, wherein the primary elastic element is a helical spring.

3. The electronic pill according to claim 1 wherein the actuator moves the mechanism from the constraining configuration to the releasing configuration upon receiving of an external trigger.

4. The electronic pill according to claim 3, comprising a primary module and a secondary module, wherein the primary module is configured for accommodating at least the primary elastic element, the mechanism and the reservoir, wherein the secondary module is arranged for accommodating at least the actuator, and wherein the primary module and the secondary module are mutually releasably connectable.

5. The electronic pill according to claim 3, comprising a sensor for measuring a body parameter and for generating the external trigger in response thereto.

6. The electronic pill according to claim 1, wherein the mechanism comprises a secondary elastic element.

7. The electronic pill according to claim 6, wherein the secondary elastic element is a leaf spring.

8. The electronic pill according to claim 7, comprising an inclined plane moveable relative to the leaf spring and connected slideable thereto and configured for inducing a predefined level of stress in the leaf spring in the constraining configuration, and upon moving due to actuation, for releasing said predefined level of stress from the leaf spring.

9. The electronic pill according to claim 8, wherein the inclined plane is connected to the threaded nut.

10. The electronic pill according to claim 1, wherein the mechanism comprises a lever for changing from the constraining configuration to the releasing configuration, wherein a first extremity of the lever is configured for temporarily constraining the piston and wherein a second extremity of the lever is configured for being actuated.

11. The electronic pill according to claim 10, wherein a distance between the first extremity and a pivot point associated with the lever is substantially smaller than a further distance between the second extremity and said pivot point.

12. The electronic pill according to claim 10, wherein the second extremity is connected to a movable nut which is driveable by the actuator.

13. The electronic pill according to claim 1, wherein the actuator is movable along a longitudinal axis of the electronic pill.

14. The electronic pill according to claim 13, wherein movement of the actuator along the longitudinal axis causes a radial movement of the mechanism between the constraining configuration and the releasing configuration.

15. An electronic pill comprising:
a reservoir containing a substance;
a piston movable along a longitudinal axis to increase a pressure in the reservoir to force the substance out of the reservoir;
a primary elastic element arranged to apply a pressure to the piston sufficient to increase the pressure in the reservoir to force the substance out of the reservoir;
a mechanism actuatable between a constraining configuration holding the piston in a constrained position that deforms the primary elastic element and a release configuration in which the deformed primary elastic element drives the piston to increase the pressure in the reservoir to force the substance out of the reservoir;
an actuator comprising a threaded shaft; and
a threaded nut engaging the threaded shaft and acting on the mechanism, the threaded nut being movable along a longitudinal axis of the pill between a first position and a second position, the second position being spaced from the first position, wherein, in the first position, the threaded nut retains the mechanism in the constraining configuration and, in the second position, the threaded nut causes the mechanism to move to the release configuration,
wherein, in the constraining configuration, a portion of the mechanism obstructs movement of the piston along the longitudinal axis and, in the releasing configuration, the portion of the mechanism moves to no longer obstruct the movement of the piston.

16. The electronic pill of claim 15, wherein the primary elastic element is a helical spring.

17. The electronic pill of claim 15, wherein the mechanism comprises a leaf spring.

18. The electronic pill of claim 17, wherein the portion of the mechanism that obstructs movement of the piston comprises a plug at a distal end of the leaf spring.

19. The electronic pill of claim 15, wherein the mechanism comprises a lever for changing from the constraining configuration to the releasing configuration, wherein a first extremity of the lever is the portion of the mechanism that obstructs movement of the piston in the constraining configuration and wherein a second extremity of the lever is configured for being actuated.

20. The electronic pill of claim 15, wherein the movable nut includes an inclined surface.

* * * * *